United States Patent [19]
West

[11] Patent Number: 4,861,164
[45] Date of Patent: Aug. 29, 1989

[54] APPARATUS FOR SEPARATING SPECULAR FROM DIFFUSE RADIATION

[75] Inventor: Robert N. West, Chislehurst, United Kingdom

[73] Assignee: SIRA Limited, Chislehurst, United Kingdom

[21] Appl. No.: 271,396

[22] Filed: Nov. 10, 1988

Related U.S. Application Data

[62] Division of Ser. No. 88,659, Aug. 24, 1987, abandoned.

[30] Foreign Application Priority Data

Sep. 5, 1986 [GB] United Kingdom ................. 8621418

[51] Int. Cl.$^4$ ..................... G01N 21/47; G01N 21/55; G01N 21/88
[52] U.S. Cl. .................................. 356/445; 356/237; 356/446
[58] Field of Search ............... 356/429, 430, 431, 445, 356/446, 448, 237

[56] References Cited

U.S. PATENT DOCUMENTS 4,629,319 12/1986 Clarke et al. ..................... 356/237
4,664,516 5/1987 Coppa et al. ..................... 356/73.1

FOREIGN PATENT DOCUMENTS 0182471 5/1986 European Pat. Off. .
5646433 7/1981 Japan .
0248790 11/1986 Japan ................................. 356/121

Primary Examiner—F. L. Evans
Attorney, Agent, or Firm—Christie, Parker & Hale

[57] ABSTRACT

An optical inspection system for determining various features of, for example, painted surfaces, by analyzing light reflected from the surface in a plurality of ways. In one case the cross sectional diameter of a beam of radiation, which gives information regarding the surface, is measured by passing the beam through a filter means (104) having transmissive and absorptive portions (107,108), the arcuate width at each radial distance from the optical axis (100) being such that there is a predetermined relationship between the diameter of the beam and the mount of radiation passed by the filter.

18 Claims, 3 Drawing Sheets

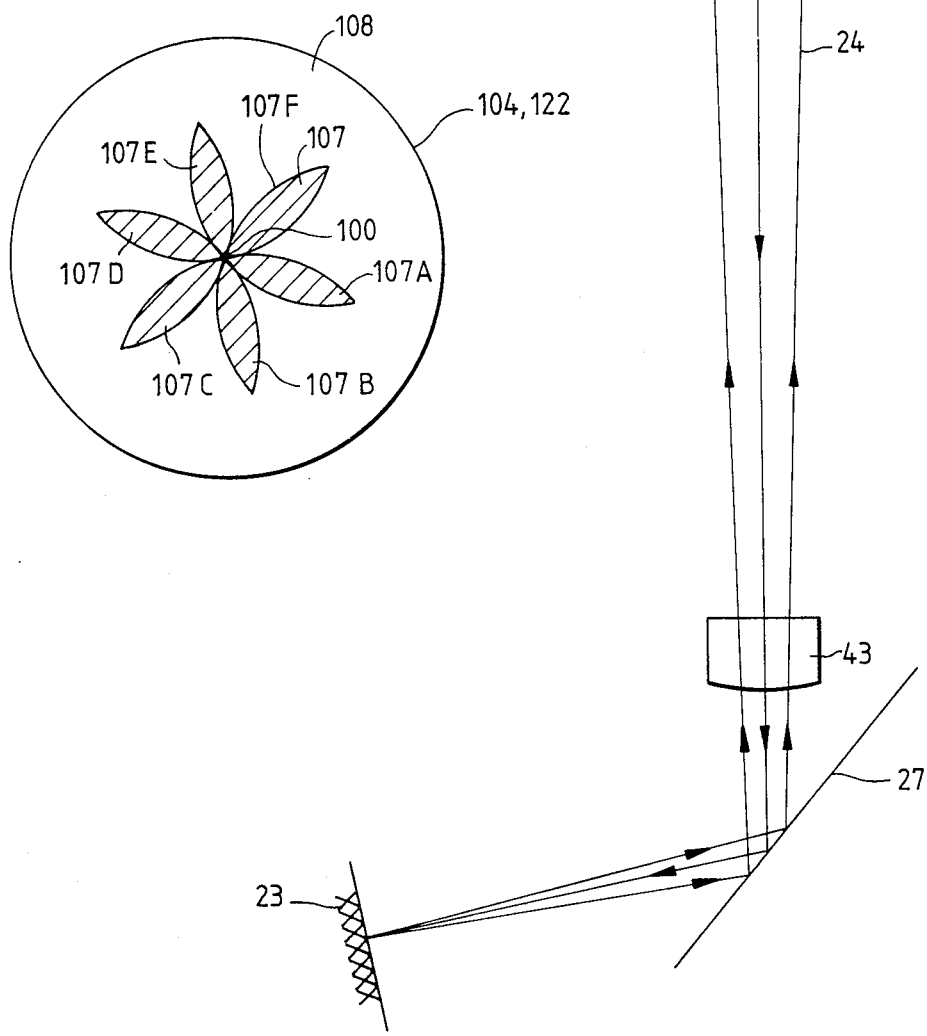

APPARATUS FOR SEPARATING SPECULAR FROM DIFFUSE RADIATION

CROSS-REFERENCE TO RELATED APPLICATIONS

This is a division of application Ser. No. 088,659, filed Aug. 24, 1987, now abandoned.

The present invention relates to an inspection apparatus which may be particularly useful in inspecting surfaces. Furthermore, a preferred embodiment of the apparatus of the invention will be particularly useful with apparatus described in our copending international patent application PCT/GB86/00399.

Although the apparatus will have applications elsewhere the inspection apparatus according to the invention will be described with reference to a particular apparatus which has been designed for use in inspecting surfaces, for example, painted or coated surfaces and is particularly useful in examining complex shaped surfaces such as the painted surfaces of motor cars, domestic appliances and the like.

Automatically inspecting complex shaped surfaces for example on a motor car production line, is extremely difficult and as a result the inspection has hitherto been carried out by human inspectors. Apart from the costs involved, the conditions under which the inspectors work is often unpleasant both as to the environment and as to the tedious nature of the job. Furthermore, although the human eye is very good at detecting defects, in practice it is not easy to arrange for a reliable and consistent classification of defects.

Through the specification we will refer to "light" and "optical". It will be understood, however, that this invention is not restricted to the use of optical wavelengths, but may be used with radiation of other wavelengths, for example, infra red or ultra violet.

The present invention provides apparatus for measuring the cross sectional diameter of a beam of radiation comprising filter means, radiation detector means, means for passing said beam via said filter means to said radiation detector means, characterised in that said filter means has an optical axis, and transmissive and reflective portions, or transmissive and absorptive portions, or reflective and absorptive portions, each of said portions having an arcuate width at each radial distance from said optical axis such that there is a predetermined relationship between the diameter of the beam and the amount of radiation passed or reflected by said filter means.

A preferred embodiment of the invention will now be described by way of example only and with reference to the accompanying drawings in which:

FIG. 2 is a side diagramatic view of part of the apparatus of FIG. 1 and,

FIG. 3 is a diagramatic view of a filter for use in the apparatus of FIG. 1.

Figure 1:
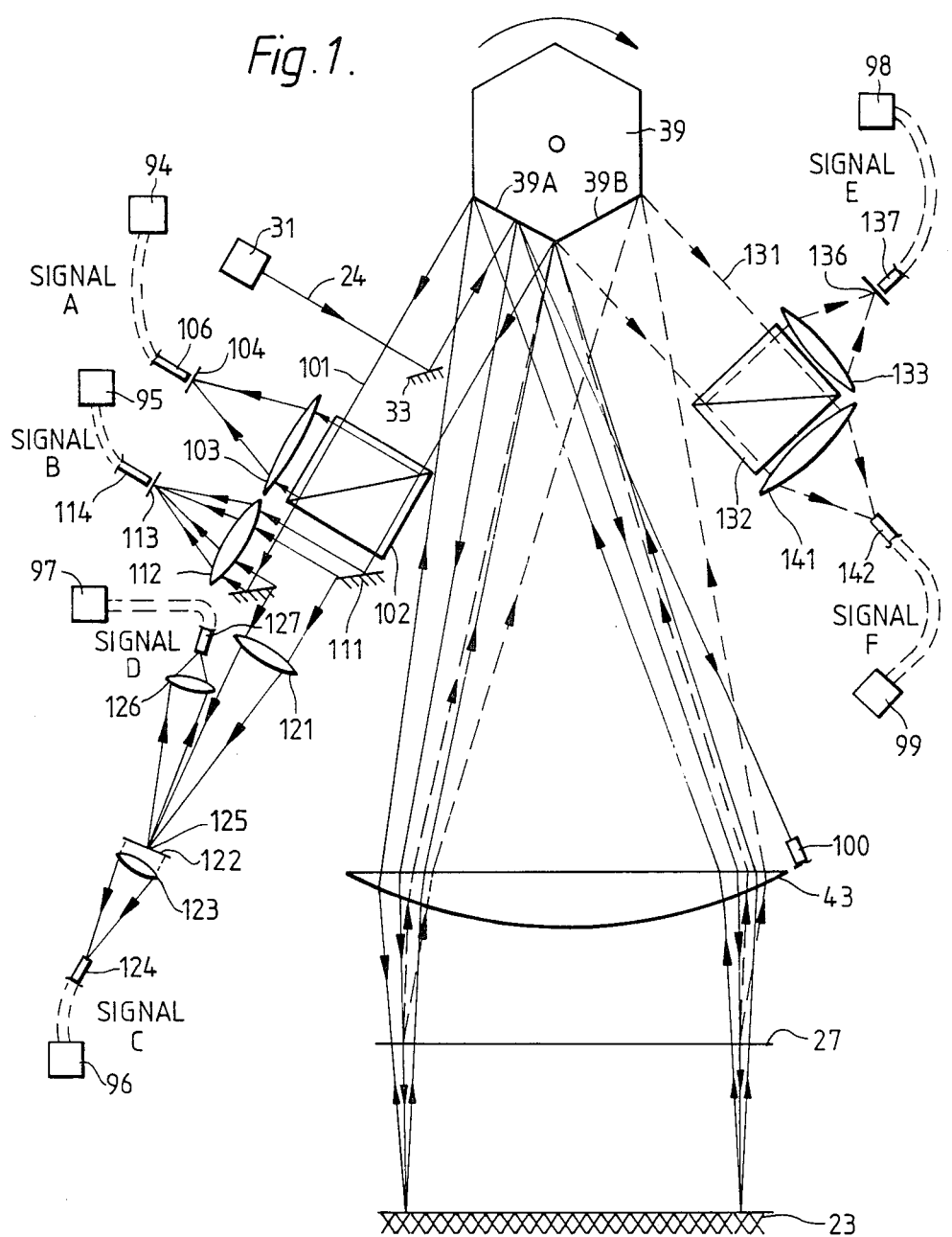
FIG. 1 is a front diagramatic views of apparatus according to the invention.

In general terms, the apparatus as disclosed in the drawings may be used to replace the scanning head 22 of the apparatus disclosed in our copending international application No. PCT/GB86/00399. The relevant parts of the description of that earlier patent application are hereby incorporated in this specification.

The apparatus comprises a laser 31 producing a laser beam 24, there being included optical components similar to the lenses 36–38 of the earlier patent application which focus the beam 24 onto a surface 27 to be inspected. The surface to be inspected may comprise the surface of a motor car. The beam 24 is reflected by means of a mirror 33 to a 8 sided polygon scanner mirror 39 which is rotated by a motor (not shown) at 20,000 RPM to give 2,666 scans per second. The scanned part of the beam is passed to an aspheric acrylic lens 43 to collimate the laser beam so that the scan length is constant in any direction from the surface 27 and also so as to allow a smaller retroreflective screen to be used compared with a diverging scan.

The laser beam 24 is then scanned across the surface 27 and is reflected from the surface 27. The light reflected from the surface 27 will comprise two components, a specular component and a diffuse component. The specular component leaves surface 27 with a small, substantially zero cone angle but the diffuse component has a large, substantially 180° cone angle. The reflected light from surface 27 strikes a retroreflective screen 23 and returns back in the incident direction to be rereflected at the surface 27 and passes through the lens 43 to the scanning drum 39. As is well known, the retroreflective screen will return a beam which is slightly divergent with respect to the beam incident on it so the specular component is reflected as a beam with a small cone angle.

The beam which has been reflected by the retroreflector 23 and reaches the facet 39A (which is the same facet as reflected the beam on its outward path) is reflected by the facet 39A. The beam reflected by the facet 39A will include both the specular component and some of the diffuse light. This beam is thus reflected by the facet 39A along an optical path 101. Because the same facet reflects the beam on its outward path as its inward path the reflected beam will be "descanned" so that movement of the beam caused by rotation of the mirror drum will be removed and thus the optical path 101 of the reflected beam will be parallel to the beam 24 passing between the mirror 33 and the facet 39A. As will be understood, the mirror 33 is small and, therefore, does not interrupt very much of the light passing along light path 101.

Thus to repeat, optical path 101 passes a beam which includes substantially all of the specular component and a proportion of the diffuse component of the beam incident on the mirror drum from the surface 27 and all movement of the beam caused by the mirror drum will be removed by reflecting back from the same facet 39A. It will also be understood that the specular component of the light will be polarised whereas the diffuse component will not be polarised.

Along the light path 101 there are provided a plurality of optical apparatus for acting on the light reflected from facet 39A. The first apparatus comprises a polarising beam splitter 102. The polarising beam splitter 102 is arranged so that the polarised specular component of the beam passes straight through the polarising beam splitter 102 whereas some (approximately half) of the diffuse component is reflected by polarising the beam splitter to a lens 103. The reflected component passes through the lens 103 onto a filter 104. Lens 103 is arranged so as to focus the surface 27 onto the filter 104 so that the filter 104 receives an image of the light beam where it strikes the surface 27. Because only diffuse light is passed to filter 104, it does not receive any light from the retroreflector 23. Filter 104 is arranged in front of a light collecting means in the form of a fibre optic 106 connected at its remote end to a light detector in the form of a photo cell 94. The filter is of the shape shown in FIG. 3.

The filter illustrated in FIG. 3 comprises a petal shaped pattern arranged symmetrically about the optical axis 100 of the filter 104. The "petals" part 107 is transmissive to the incident radiation and comprises six petals 107A,B,C,D,E,F and the surrounding part 108 is absorptive of the incident radiation. Although in other situations the two parts can be transmissive and reflective (see later with respect to filter 122), or reflective and absorptive of the radiation. The shape of the two parts 107,108 can be clearly seen from FIG. 3, each of said parts 107,108 extending from the optical axis 100. Importantly, each of said parts 107,108 (part 107 comprising the sum of petals 107A-F) has a predetermined arcuate width at each radial distance from the optical axis 100 to provide a predetermined relationship between the diameter of the beam and the amount of radiation passing through the filter.

The effect of the filter can be simply explained as follows. Assuming that the light passing through the lens 103 is constant, then the diameter of the beam at the filter 104 can be determined by measuring the amount of light passing through the petal parts 107A-F. If the beam is focused to a small spot on the optical axis 100 of filter 104, then all of the light will pass through the transparent part of the petal parts 107A-F to the fibre optic 106. As the diameter of the beam focused on filter 104 increases then an increasing proportion of the light is absorbed by the opaque part 108 between each petal 107A-F and thus an increasing proportion of the light is lost and not passed to the fibre optic 106. The shape of the petals 107A-F is arranged so that the light passed through to the fibre optic 106 is substantially linearly dependent upon the diameter of the beam at the filter 104. In practice we have found a relationship which is linear to ±5% or even ±1% relatively easy to achieve, but in some cases +20% might be sufficient.

In other cases one might prefer to have other predetermined relationships. For example, one might prefer to provide greater changes of output signal over small diameter changes at a particular diameter of interest, with smaller changes of output signal being sufficient at other diameters of less interest.

Although the part 107 is illustrated in the preferred embodiment as comprising six petals 107A-F. However, other shapes are possible. The requirement is that each of the parts 107,108 has a predetermined arcuate width at each radial distance from the optical axis. This may be provided, for example, by a generally cusp shaped part 107. The focus of the cusp extending to the optical axis 100 or may be provided by petals 107A-F in which segments of the petals are displaced with respect to petal parts which are of lesser and greater radial distance from the optical axis 100. This affect could be provided, for example, by a chequer board pattern.

Furthermore, although the preferred embodiment provides a separate filter 104, the filter of the invention may be provided by the shape of the front surface of a photodetector or fibre optic 106. Thus, for example, in place of filter 104, the front face of the fibre optic 106 may, if desired, be shaped like the part 107, that is it may be petal shaped so as only to collect light from an area corresponding to the petals 107A-F (or any of the alternatives described above) and thus the word "filter" in respect of the claims should be interpreted accordingly, to include the shape of the light collecting face of the fibre optic or of a photodetector.

We will refer to the signal produced by the light sensitive device at the remote end of the fibre optic 106 as signal A.

Signal A is, therefore, a measure of diffuse light only (back scattered light) directly from the surface 27 which has not passed via the retroreflector 23. The outward beam 24 is focused by optical components (not shown) so as to be focused onto surface 27 when the distance between the scanning head and surface 27 is at its optimum distance. If that distance varies, then the image on the surface 27 moves out of focus and so its diameter changes. This is, of course, indicated by signal A, which is proportional to the diameter of the image on the filter 104. Thus, signal A is a measure of the distance between the lens 43 and surface 27.

Although this works well in practice, there are some difficulties, because it is not then possible to tell whether the distance between lens 43 and 27 is decreasing or increasing, since it will be moving out of focus and, therefore, the image will be increasing in size in both directions and so, we may arrange the focus to be either in front of or behind the normal maximum position of the surface 27 with respect to the lens 43 so that an increase in the diameter will indicate movement in one direction and a reduction in diameter will indicate movement in another direction.

However the light reaching the optic fibre 106 is not only dependent upon the diameter of the spot focused on filter 104 but is also dependent upon the actual amount of light in the beam passed to the filter 104 and this can vary depending upon the surface which is being scanned. To eliminate this effect it is necessary to normalise the signal A by comparing the signal A with a signal which is simply dependent upon the diffuse light. This is carried out by comparing signal A with signal F to be described later.

Light which passes through the beam splitter 102 is passed to an annular mirror 111. Light reflected by the annular mirror 111 is passed by a lens 112 to a filter 113 behind which is mounted a fibre optic 114 for collecting light passing through the filter 113 and passing this light to a remote light sensitive device (not shown). The signal produced by this light sensitive device will be referred to as signal B. Lens 112 focuses an image of the retroreflector 23 onto the filter 113. Filter 113 comprises a clear disc with a matt black centre or may comprise a bundle of separate fibre optics disposed around the matt black centre and being connected to a plurality of remote light sensitive devices 95 or may comprise a plurality of light sensitive devices spaced about a matt black centre.

Signal B is a measure of movement of the spot of light on the retrorefecting surface 23 which is caused by small defects. If there are small defects on the surface 27 which cause deflection of the beam, then the spot on the retroreflector 23 will be moved. Because the reflected light from the retroreflector 23 has a certain cone angle, if the defect causing the movement of the spot is small compared with the diameter of the beam when it returns from the retroreflector 23 to the surface 27, then the bulk of the light returning from the retroreflector 23 to the surface 27 will not strike the same defect, but will strike an area around that defect and will be reflected back to the lens 43 in a different direction from the incident beam from lens 43 to surface 27. This movement of the spot of light on the retroreflector 23 will therefore be picked up by the filter 113 and signal B will be a measure of this movement. In terms of a painted panel of a motor car, the kind of defect which would be indicated by signal B is so called "orange peel" that is, small variations in the surface of the paint. Similarly, surface defects such as scratches and digs will produce diffracted light which will be outside the matt black central spot on the filter and so will be detected by signal B.

Light passing through the annular mirror 111 is passed by a lens 121 onto a filter 122 which is similar to filter 104 except that it includes a matt black centre 125 on its optical axis to absorb the light and the part 108 is of reflective material. Lens 121 actually focuses surface 27 onto filter 122. Light passing through the transparent petal parts 107 is collected by a lens 123 and focused on a fibre optic 124 connected at its remote end to a light sensitive device 96 which provides a signal C. Light reflected from the reflective part 108 is collected by a lens 126 and focused on a fibre optic 127 having a light sensitive device 97 remotely connected thereto to provide a signal D. Because lens 121 focuses the surface 27 onto the filter 122 and because the diffuse light originates from the surface 27, all of the diffuse light is therefore focused to a central point on the filter 122 and is eliminated by the matt black central spot. Thus, only specular light is received by the outer part of the filter 122 and is either passed through to fibre optic 124 or is reflected to fibre optic 127 to produce signals C and D respectively. The sum of signals C and D therefore provides a measure of the total specular light. Signal C will indicate the diameter of the spot of specular light incident on the filter 122 and this provides measurements of subtle changes of the shape of the surface 27. If there are slight changes of shape of the surface 27 then, so far as the specular light is concerned, the surface 27 will act as an active optical component either focusing or defocusing the slightly divergent beam or light which is reflected from the retroreflector 23 to the surface 27. Thus, by ratioing the signals C and D we provide a measure of the diameter of the image at filter 122 which in turn is an indication of the curvature and hence the optical power of the surface 27. This measurement is particularly useful, since it will measure very shallow dents on near flat panels which are otherwise difficult to detect.

As has already been indicated, diffuse light is reflected from the surface 27 through a cone angle of 180° and, therefore, some of this diffuse light will pass back and reach the facet 39B adjacent to the facet 39A. In practice, a small amount of specular light will also reach facet 39B. The light received by facet 39B is reflected along an optical path 131. The optical path 131 is substantially stationary and it is "descanned" in the same was as optical path 101. However, because the facets 39A and 39B are not in exactly the same position there is some slight movement of the optical path 131.

Light on the optical path 131 passes to a polarising beam splitter 132. Light reflected by the polarising beam splitter 132 is collected and focused by lens 133 and focused onto a slit 136, light passing through the slit 136 being collected by a fibre optic 137 connected at its remote end to a light sensitive device 98 to provide a signal E. The lens 133 focuses an image of the retroreflectors surface 23 onto the slit 136. The signal E is a measurement of a characteristic of the surface 27 which is referred to as "distinctness of image" (DOI). This is essentially how clear the image of an object appears when viewed via the surface 27 and is of interest in respect of painted surfaces such as motor cars.

As the beam 24 is scanned across the surface 27 the image of the retroreflector 23 on the filter 136 will move slightly during each scan and hence will slowly scan across the slit 136. In practice two images reach the slit 136, a first focused image of the beam at the retroreflector surface 23 and a second image of the beam at the surface 27. These two images are separated spatially and signal E relates only to the scanning of the image of the beam on the retroreflector surface 23 across the slit.

By selecting the signal from the retroreflector 23 the DOI can be measured as the sharpness of the signal edges when compared with the width of the spot (in other words a measure of the degree of fuzziness of the edge of the spot). An analysis of the signal E during a scan will produce a measurement of this fuzziness and hence the DOI.

Light passing through the polarising beam splitter 132 is focused by a lens 141 directly onto a fibre optic 142 the remote end of which is connected to a light sensitive device 99 to provide a signal F.

As indicated above the light passing along the light path 131 is diffuse light and so the signal F is a direct measure of the diffuse light. As indicated earlier with respect to signal A, signal F provides a normalisation signal. In other words, as the diffuse light reflected by the surface 27 varies, for example due to changes of colour or other effects, signal A will vary because the total amount of light striking the filter 104 will vary, but this effect can be removed by comparing signal A with signal F which will also vary in the same way.

Furthermore, on very steeply curved surfaces where the specularly reflected light from surface 27 does not pass to the retroreflective screen 23, severe surface defects can also be detected by means of changes in the diffuse light passed along light path 131 and indicated by changes in signal level F. In this way, therefore, on steeply curved surfaces, for example, bumpers or folded edges around wheel arches, defects such as dents in those surfaces may be detected by the signal F.

Various features of the surface and other matters may be determined by a signal analyser (not shown) by considering and comparing various of the signals A to F.

A combination of signals A and F, (for example the ratio of signals A to F) will provide a measure of the distance between the scanning head and the surface 27. The rate of change of this range can be used to provide a measure of surface curvature.

Changes in the level of signal F can be used indicate diffuse defects such as changes of surface colour. On very steeply curved surfaces where no specular return can be obtained from the retroreflective screen 23 (i.e. the beam from the surface 27 misses the screen 23) severe surface defects can be detected.

Summing signals C and D provides an indication of surfaces defects such as dinks, dirt nibs, and low gloss.

By comparing signals C and D (preferably by providing the ratio signals C to D) shallow dents or bulges in flat panels can be detected.

Signal B measures surface defects such as "orange peel" or scratches or digs.

Signal E measures the distinctiveness of image (DOI).

Beyond one end of the lens 43 is provided a bundle 100 of fibre optics. The opposite ends of the fibre optics 100 may be arranged to pass light to the various detectors which produce signals A to F whereby to compensate for variations in the laser light level or sensitivity of the light detectors.

I claim:

1. Apparatus for separating specular from diffuse radiation from an area of a surface under inspection, comprising means for passing radiation to said surface, retroreflective means positioned with respect to said surface for reflecting radiation from said surface back to said surface, focusing means for receiving radiation from said surface, and filter means having a first central area on its optical axis and a second surrounding area, said filter means and the area of said surface under examination being conjugate with respect to the focusing means whereby all of said diffuse radiation from said area of said surface under inspection is passed to said central area of said filter means and specular radiation from said area of said surface under inspection is passed to said second surrounding area so that said specular and said diffuse radiation are separated.

2. Apparatus as claimed in claim 1 in which said surrounding area of said filter means is sub-divided into two further areas, one of said further areas of said filter means is reflective to said radiation and the other is transmissive, and further comprising respective radiation detector means placed in such positions to receive radiation reflected by said one area and transmitted by said other area.

3. Apparatus as claimed in claim 1 in which one of said areas of said filter means is absorptive of said radiation and the other is transmissive of said radiation and further comprising a radiation detector means placed in such a position as to detect radiation transmitted by said other area.

4. Apparatus as claimed in either of claims 2 or comprising means for normalizing a signal provided by said radiation detector means to take into account other variations of the amount of radiation received by the filter means.

5. Apparatus as claimed in claim 4 in which said means for normalizing the signal comprises means for collecting radiation direct from a radiation source providing said radiation without being influence by said surface under inspection.

6. Apparatus as claimed in claim 1 including means for scanning the area of said surface under inspection across a surface.

7. Apparatus as claimed in claim 6 in which said means for scanning said area of said surface under inspection comprises a mirror drum scanner.

8. Apparatus as claimed in claim 2 including means for scanning the area of said surface under inspection across a surface.

9. Apparatus as claimed in claim 8 in which said means for scanning said area of said surface under inspection comprises a mirror drum scanner.

10. Apparatus as claimed in claim 3 including means for scanning the area of said surface under inspection across a surface.

11. Apparatus as claimed in claim 10 in which said means for scanning said area of said surface under inspection comprises a mirror drum scanner.

12. Apparatus as claimed in claim 4 including means for scanning the area of said surface under inspection across a surface.

13. Apparatus as claimed in claim 12 in which said means for scanning said area of said surface under inspection comprises a mirror drum scanner.

14. Apparatus as claimed in claim 5 including means for scanning the area of said surface under inspection across a surface.

15. Apparatus as claimed in claim 14 in which said means for scanning said area of said surface under inspection comprises a mirror drum scanner.

16. Apparatus as claimed in claim 1 in which one of said areas of said filter means is reflective to said radiation.

17. Apparatus as claimed in claim 1 in which one of said areas of said filter means is transmissive of said radiation.

18. Apparatus as claimed in claim 1 in which one of said areas of said filter means is absorptive of said radiation.

* * * * *

UNITED STATES PATENT AND TRADEMARK OFFICE
CERTIFICATE OF CORRECTION

PATENT NO. : 4,861,164
DATED : August 29, 1989
INVENTOR(S) : Robert N. West

It is certified that error appears in the above-identified patent and that said Letters Patent is hereby corrected as shown below:

On the Front Page:

Abstract, line 11, change "mount" to -- amount --.
Front Page, change "3 drawing sheets" to -- 2 drawing sheets --.

In the Specification

Column 3, line 40, change "+" to -- $\pm$ --.

Column 5, line 38, change "or" to -- of --. (2nd occurr)
Column 5, line 55, change "was" to -- way --.

Column 6, line 51, before "indicate" insert -- to --.

Column 7, line 35, change "2 or" to -- 2 or 3 --.

Column 8, line 1, change "influence" to -- influenced --.

Signed and Sealed this

Twentieth Day of November, 1990

Attest:

HARRY F. MANBECK, JR.

Attesting Officer

Commissioner of Patents and Trademarks